United States Patent
Kroger Lyons et al.

(10) Patent No.: US 10,653,609 B2
(45) Date of Patent: May 19, 2020

(54) METHOD OF CLEANING HAIR USING A LOW PH HAIR CARE COMPOSITION

(71) Applicant: The Procter & Gamble Company, Cincinnati, OH (US)

(72) Inventors: Kelly Rose Kroger Lyons, Liberty Township, OH (US); Mikah Coffindaffer, Mason, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 413 days.

(21) Appl. No.: 15/448,741

(22) Filed: Mar. 3, 2017

(65) Prior Publication Data
US 2017/0252284 A1  Sep. 7, 2017

Related U.S. Application Data

(60) Provisional application No. 62/302,869, filed on Mar. 3, 2016.

(51) Int. Cl.
| | | |
|---|---|---|
| *A61Q 5/02* | (2006.01) | |
| *A61K 8/81* | (2006.01) | |
| *A61Q 5/12* | (2006.01) | |
| *A61K 8/44* | (2006.01) | |
| *A61K 8/46* | (2006.01) | |
| *A61Q 5/00* | (2006.01) | |

(52) U.S. Cl.
CPC ............ *A61K 8/8182* (2013.01); *A61K 8/442* (2013.01); *A61K 8/463* (2013.01); *A61K 8/8152* (2013.01); *A61K 8/8158* (2013.01); *A61K 8/8188* (2013.01); *A61Q 5/00* (2013.01); *A61Q 5/02* (2013.01); *A61Q 5/12* (2013.01); *A61K 2800/30* (2013.01); *A61K 2800/34* (2013.01); *A61K 2800/48* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 4,321,156 A | 3/1982 | Bushman | |
| 5,137,715 A | 8/1992 | Hoshowski et al. | |
| 5,661,118 A * | 8/1997 | Cauwet | A61K 8/442 |
| | | | 510/126 |
| 5,804,207 A | 9/1998 | Dubief et al. | |
| 7,025,973 B2 | 4/2006 | Loeffler | |
| 7,534,272 B2 | 5/2009 | Cassier et al. | |
| 7,709,430 B2 | 5/2010 | Mizushima | |
| 8,632,758 B2 | 1/2014 | Terada | |
| 8,680,032 B2 | 3/2014 | Lachmann | |
| 9,554,979 B2 | 1/2017 | Combs et al. | |
| 2004/0166084 A1 | 8/2004 | Sakai et al. | |
| 2006/0040837 A1 | 2/2006 | Frantz et al. | |
| 2007/0224152 A1 | 9/2007 | Sakai et al. | |
| 2012/0022037 A1 | 1/2012 | Terada | |
| 2012/0177709 A1 | 7/2012 | Frantz et al. | |
| 2012/0183479 A1 | 7/2012 | Loeffler | |
| 2013/0174863 A1 | 7/2013 | Marsh et al. | |
| 2014/0093466 A1 | 4/2014 | Combs et al. | |
| 2014/0094423 A1 | 4/2014 | Terada | |
| 2014/0288191 A1 | 9/2014 | Kim et al. | |
| 2015/0044156 A1 | 2/2015 | Schulze zur Wiesche et al. | |

FOREIGN PATENT DOCUMENTS

JP  2009234960 A  10/2009

OTHER PUBLICATIONS

PCT International Search Report and Written Opinion for PCT/US2017/020336 dated May 24, 2017.
"Get in touch with performance—Aristoflex polymers: Rheology Modifiers and Polymeric Emulsifiers", Dr. Peter Klug, Industrial & Consumer Specialties, CC Personal Care, Clariant, Jan. 27, 2010, 34 pages.
"Aristoflex AVC", Industrial & Consumer Specialties, Clariant International Ltd., Jan. 2010, 3 pages.
"Aristoflex AVC", Safety Data Sheet, Clariant, Version 4-3, Revision Date: Nov. 30, 2015, Date of Printing Dec. 28, 2015, 11 pages.
"Carbopol Aqua SF-1 Polymer", Safety Data Sheet, Lubrizol Advanced Materials, Inc., Revision Date: Feb. 19, 2016, 9 pages.
"Carbopol Aqua SF-1 Polymer", Product Summary Sheet, Lubrizol Advanced Materials, Inc., Jun. 2006, 2 pages.
"Carbopol Aqua SF-1 Polymer", INCI Name: Acrylates Copolymer, Technical Data Sheet, Lubrizol Advanced Materials, Inc., Feb. 7, 2013, 9 pages.
"Sepigel 305—Emulsifying-thickening polymer—A formulator's essential partner", Seppic, 38 pages.
"Sepigel 305", Safety Data Sheet, Seppic, Nov. 22, 2010, 7 pages.
"Sepigel 305", Statement 10 138 04 Composition File, Seppic, Oct. 30, 2013, 2 pages.
"SepiMAX Zen", Seppic, Oct. 3, 2010, 29 pages.
"Luvigel Star", BASF, BeautyCare Ingredients, 6 pages.
"Luvigel Star", Technical Information, Personal Care Ingredients, BASF, Apr. 2009, 18 pages.
"Luvigel Star", Formulation guide, BASF, Apr. 1, 2009, 36 pages.
"Salcare SC 96", Safety Data Sheet, BASF, Sep. 29, 2016, 10 pages.
Aculyn 46N Rheology Modifier/Stabilizer, Technical Data Sheet, The Dow Chemical Company, 5 pages.
"Aculyn 46 Rheology Modifier/Stabilizer" An Efficient Shear Thinning Compatible with Cationics, Material Data Safety Sheet, The Dow Chemical Company, Apr. 2004, 7 pages.

(Continued)

*Primary Examiner* — Jyothsna A Venkat
(74) *Attorney, Agent, or Firm* — Angela K. Haughey

(57) ABSTRACT

A method of using a hair care composition that cleans the hair and removes dirt and product build up, while also leaving the hair feeling clean, lightly conditioned and/or untangled, as demonstrated by the wet combing and hair feel tests. The hair care composition includes a surfactant, a rheology modifier, and an aqueous carrier, wherein the composition has a pH ranging from about 2 to about 4 as measured by taking a direct pH measurement using a standard hydrogen electrode of the composition at 25° C. Additionally, the viscosity of the aqueous composition is from about 3,000 cP to about 15,000 cP.

2 Claims, 2 Drawing Sheets

(56) References Cited

OTHER PUBLICATIONS

"Aculyn 44", Safety Data Sheet, The Dow Chemical Company, Revised Feb. 7, 2012, 9 pages.
"Aculyn 44 Rheology Modifier/Stabilizer", An Excellent Thickener for Inorganic Sunscreen Formulations, Material Data Safety Sheet, The Dow Chemical Company, Apr. 2004, 8 pages.
"Sepimax Zen", Safety Data Sheet, Seppic, Nov. 24, 2010, 7 pages.
"Salcare SC 96 Rheology Modifier", Technical Data Sheet, BASF, Jan. 2010, 4 pages.
"Luvigel STAR", Personal Care Ingredients, Safety Data Sheet, BASF, Jun. 16, 2010, 6 pages.

* cited by examiner

METHOD OF CLEANING HAIR USING A LOW PH HAIR CARE COMPOSITION

BACKGROUND OF THE INVENTION

The present invention relates to a deep cleansing hair care composition and method that provide good in-use experience and superior hair benefits when dry.

BACKGROUND OF THE INVENTION

Typically, clarifying shampoos are employed to provide a high level of cleaning for hair, good lather and clean rinse feel. However, such shampoos are perceived to strip the natural moisturizers from the hair fibers, as they result in high wet hair friction that is translated into poor wet feel and high dry hair friction that is translated into poor, non-moisturized dry hair feel. The poor wet feel and high dry hair friction are particularly noticeable in the case of consumers that have chemically or physically damaged hair resulting from permanent or semi-permanent styling treatments, oxidative coloring treatments, thermal treatments, etc. To remedy the feeling of poor wet feel and high dry hair friction, consumers often turn to traditional conditioning shampoos which can provide good wet and dry hair feel. However, many of these products do not possess strong cleansing ability, they generate lower volume of lather during use, they do not provide clean rinse feel and they can allow more soils, sebum and other residues to remain on the hair after shampooing. In addition, the conditioning agents themselves can contribute to the feeling of residue that is added on the hair surface during the shampoo and/or conditioner process that they may accumulate in each cycle. This can result in hair weigh-down hair with low volume that is perceived as greasy, and that may also be perceived by the consumer as lanky, non-bouncy and difficult to style. Thus, there is a need for the development of shampoo compositions that provide strong cleansing ability and at the same time contribute to hair feeling clean, lightly conditioned, and untangled.

Described herein is a deep cleansing hair care composition that enables a thorough removal of soils such as sebum, conditioning, styling and other residues from hair surface in order to achieve clean hair feeling lightly conditioned and untangled.

SUMMARY OF THE INVENTION

Described herein is a method of treating hair and scalp using an aqueous composition comprising; applying an aqueous composition to the hair and scalp, wherein the aqueous composition comprises: from about 0.5 to about 10% of one or more surfactants wherein the surfactant is selected from the group consisting of anionic, amphoteric, zwitterionic, nonionic and mixtures thereof; one or more rheology modifiers wherein the rheology modifier is selected from the group consisting of: a) a polymer wherein one of the monomers contains a sulfonic group, b) a polymer wherein one of the monomers is a vinylacrylamide; c) and mixtures thereof; and wherein the pH of the composition is from about 2 to about 4, and the viscosity of the aqueous composition is from about 3,000 cP to about 15,000 cP; and wherein the method of treating hair comprises the steps: leaving the aqueous composition on hair from about 4 to about 15 minutes, and rinsing the aqueous composition with water.

DETAILED DESCRIPTION OF THE INVENTION

Figure 1:
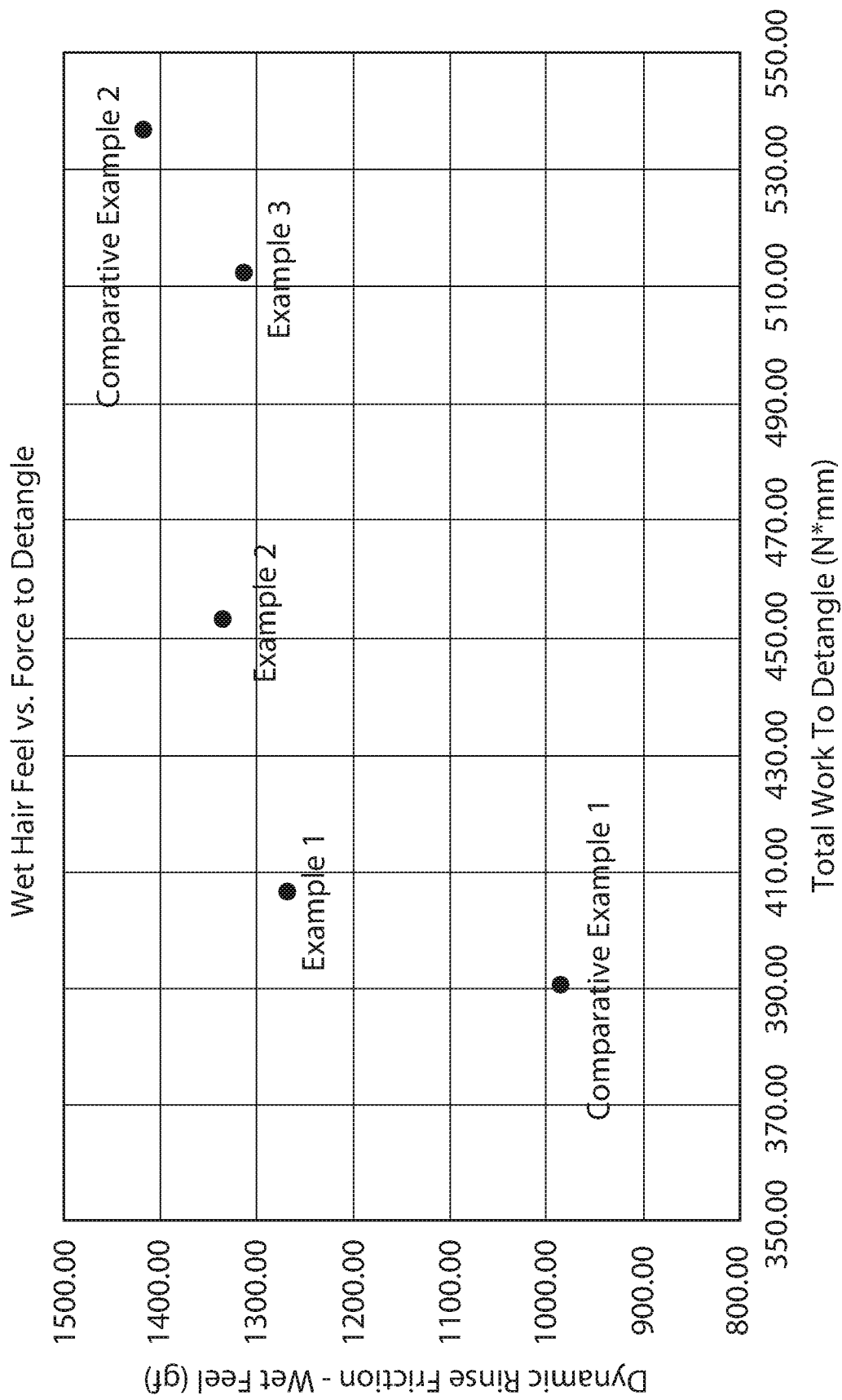
FIG. 1 is a graph showing the wet feel to the detangling force of hair samples after application of hair care compositions.

While the specification concludes with the claims particularly pointing and distinctly claiming the invention, it is believed that embodiments of the present invention will be better understood from the following description. In all embodiments of the present invention, all weight percentages are by weight of the total composition, unless specifically stated otherwise. All ratios are weight ratios, unless specifically stated otherwise. All ranges are inclusive and combinable. The number of significant digits conveys neither limitations on the indicated amounts nor on the accuracy of the measurements. All numerical amounts are understood to be modified by the word "about" unless otherwise specifically indicated. All measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

As used herein, the term "hair care compositions" are compositions that are applied to the hair and/or the skin underneath the hair, including compositions used to treat or care for the hair. Products contemplated by the phrase "hair care composition" include, but are not limited to serums, after-shave tonics and lotions, creams, emulsions, foams, hair conditioners (rinse-off and leave-on), hair colorants, hair tonics, liquids, lotions, mousses, propellant lotions, shampoos, shave gels, temporary beard hair dyes, and the like.

"Mammalian hair," as referenced herein, includes hair on any part of the body of a mammal, and can include but is not limited to facial, cranial, or body hair. For instance, it can include hair on the scalp, head, neck, beard, moustache, eyebrows and sideburns hair.

The term "topical application," as used herein, means to apply or spread the compositions of the present invention onto the surface of the keratinous tissue from which the hair to be affected grows.

The term "dermatologically-acceptable," as used herein, means that the compositions or components thereof so described are suitable for use in contact with mammalian keratinous tissue without undue toxicity, incompatibility, instability, allergic response, and the like.

The term "effective amount," as used herein, means an amount of a compound or composition sufficient to increase the diameter of the shafts in the subject region of hair by a statistically significant amount, to increase the hair density (number of hairs per area) by a statistically significant amount, and/or to delay the appearance of gray hair by a statistically significant amount.

A. Hair Care Compositions

In one aspect, the invention relates to the method of using a hair care compositions that cleans the hair and removes dirt and product build up, while also leaving the hair feeling clean, lightly conditioned and/or untangled, as demonstrated by the combing and hair feel tests. The hair care composition includes a surfactant, a rheology modifier, and an aqueous carrier, wherein the composition has a pH ranging from about 2 to about 4 as measured by taking a direct pH measurement using a standard hydrogen electrode of the composition at 25° C. Additionally, the viscosity of the aqueous composition is from about 3,000 cP to about 15,000 cP. Optionally, the hair care compositions can further comprise other dermatologically-acceptable additives and/or any desired suitable optional ingredients. The hair care composition are left on the hair for about 4 or more minutes prior to rinsing. However, this hair care composition can deliver the consumer desired conditioning, and ease of combing benefits without the use of a traditional conditioning agent like silicone. The hair care composition may be substantially free of conditioning materials including, but not limited to silicones, deposition polymers, cationic surfactants and combinations thereof. As used herein "substantially free of" means less than about 0.01 wt %, alternatively 0 wt % to about 0.01 wt %. The hair care composition can be in the form of a serum which as used herein, means a thickened hair care composition that when used according to the described method results in improved hair shine, and makes hair more manageable.

1. Surfactants

The shampoo composition may comprise one or more detersive surfactants, which provides cleaning performance to the composition. The one or more detersive surfactants in turn may comprise an anionic surfactant, amphoteric, non-ionic, zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 10 wt %, from about 1 wt % to about 9 wt %, from about 2 wt % to about 9 wt %, from about 2 wt % to about 8 wt %, and about 3 wt % to about 8 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

Suitable amphoteric or zwitterionic surfactants for use in the shampoo composition herein include those which are known for use in shampoo or other personal care cleansing. Concentrations of such amphoteric surfactants range from about 2 wt % to about 10 wt %, and from about 1 wt % to about 9 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non-ionic detersive surfactants suitable for use in the shampoo composition are selected from the group consisting of: Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PPG-2 Cocamide, PPG-2 Hydroxyethyl Cocamide, and mixtures thereof.

Non limiting examples of other anionic, zwitterionic, nonionic, amphoteric or optional additional surfactants suitable for use in the shampoo composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

2. Rheology Modifier

The composition comprises a rheology modifier for the purpose of maintaining the overall viscosity of the bulk product in a range that allows for easy spreading of the composition in the hands and on the head during the application process while also providing enough viscosity to maintain a controllable dosage when dispensing into the hand without fear of the product running or dripping before the application process is complete. According to another embodiment, the hair care composition may include one or more rheology modifiers. The rheology modifier can be selected from copolymers wherein one of the monomers is a vinylacrylamide that contains a sulfonic group. The Rheology modifiers can also be those obtained by inverse emulsion polymerization and used in a form of inverse lattices. The rheology modifier itself is present in an amount of at least from about 0.5 to about 3% wt %, from about 1, about 1.5, about 2, to about 3, about 2.5, about 2 wt %. One or more rheology modifiers may be included in the hair care composition, wherein the rheology modifier(s) can be chosen from a) a polymer wherein one of the monomers contains a sulfonic group, b) a polymer wherein one of the monomers is a vinylacrylamide; c) and mixtures thereof. The rheology modifier can be a polyacrylamide obtained by inverse emulsion polymerization and used in a form of inverse lattices. The rheology modifier can be a polyacrylate crosspolymer-6. The polymer of the rheology modifier can be a polyacrylate crosspolymer-6 or ammonium acryloyldimethyltaurate/Vinylpyrrolidone Copolymer.

Suitable rheology modifiers include Acrylamide/Sodium Acryloyldimethyl Taurate Copolymer & Isohexadecane & Polysorbate 80, Sodium Acrylate/Sodium Acryloyldimethyl Taurate Copolymer & Isohexadecane & Polysorbate 80, Sodium Acrylate/Sodium Acryloyldimethyl Taurate Copolymer (and) Polyisobutene (and) Caprylyl/Capryl Glucoside, Hydroxyethyl Acrylate/Sodium Acryloyldimethyl Taurate Copolymer (and) squalane (and) polysorbate 60, Ammonium Polyacrylate & Isohexadecane & PEG-40 Castor Oil, Polyacrylate-13 (and) Polyisobutene (and) Polysorbate 20, Polyacrylate-13 & Polyisobutene & Polysorbate 20, Polyacrylate-13 (and) Polyisobutene (and) Polysorbate 2.

Suitable commercially-available rheology modifiers include Sepigel™ 305, Simulgel™ 600, Sepimax Zen, Simulgel™ EG, Simulgel™ EPG, Simulgel™ NS, Simulgel™ A, Sepiplus™ 400, Sepiplus™ 250, Sepiplus™ 265 Aristoflex® AVC, Aristoflex® Velvet, Aristoflex® TAC, Aristoflex® HMB, Aristoflex® BLV, or Aristoflex® AVS and combinations thereof.

3. Carrier

According to another aspect of the present invention, the hair care compositions further include from about 75 to about 95%, from about 80% to about 90%, from about 85% to about 95%, from about 90% to about 95% weight percent of an aqueous carrier. The aqueous carrier may be prepared from demineralized or distilled water, for example. Other acceptable carriers that may be used in the aqueous carrier include, but are not limited to alcohol compounds, such as ethanol.

The hair care compositions have a pH ranging from about 2.0 to about 4, which may be measured by taking a direct pH measurement using a standard hydrogen electrode of the composition at 25° C. Accordingly, the pH of the hair care composition may be within the range from about 2 to about 3, alternatively from about 3 to about 4.

4. Optional Ingredients

The hair care compositions described herein may optionally comprise one or more additional components known for use in hair care or personal care products, provided that the additional components are physically and chemically compatible with the essential components described herein, or do not otherwise unduly impair product stability, aesthetics or performance Such additional components are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the hair care compositions.

Non-limiting examples of additional components for use in the hair care compositions include conditioning agents (e.g., silicones, hydrocarbon oils, fatty esters), natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, perfume microcapsules, preservatives, proteins, skin active agents, sunscreens, UV absorbers, and vitamins.

a. Conditioning Agent

The hair care compositions may comprise one or more conditioning agents. Conditioning agents include materials that are used to give a particular conditioning benefit to hair and/or skin. The conditioning agents useful in the hair care compositions of the present invention typically comprise a water-insoluble, water-dispersible, non-volatile, liquid that forms emulsified, liquid particles. Suitable conditioning agents for use in the hair care composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix.

One or more conditioning agents are present from about 0.01 wt % to about 10 wt %, from about 0.1 wt % to about 8 wt %, and from about 0.2 wt % to about 4 wt %, by weight of the composition. However, the hair care composition may be substantially free of conditioning agents, having from 0 to about 0.01% of a conditioning agent.

1) Silicones

The conditioning agent of the hair care compositions may be an insoluble silicone conditioning agent. The silicone conditioning agent particles may comprise volatile silicone, non-volatile silicone, or combinations thereof. In one embodiment the conditioning agent is a non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The dispersed silicone conditioning agent particles typically have a volume average particle diameter ranging from about 0.01 micrometer to about 50 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, from about 20 micrometer to about 50 micrometer.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

2) Organic Conditioning Oils

The conditioning agent of the hair care compositions described herein may also comprise at least one organic conditioning oil, either alone or in combination with other conditioning agents, such as the silicones described above.

3) Other Conditioning Agents
i. Quaternary Ammonium Compounds

Suitable quaternary ammonium compounds for use as conditioning agents in the hair care compositions described herein include, but are not limited to, hydrophilic quaternary ammonium compounds with a long chain substituent having a carbonyl moiety, like an amide moiety, or a phosphate ester moiety or a similar hydrophilic moiety.

Examples of useful hydrophilic quaternary ammonium compounds include, but are not limited to, compounds designated in the CTFA Cosmetic Dictionary as ricinoleamidopropyl trimonium chloride, ricinoleamido trimonium ethylsulfate, hydroxy stearamidopropyl trimoniummethylsulfate and hydroxy stearamidopropyl trimonium chloride, or combinations thereof.

ii. Polyethylene Glycols

Additional compounds useful herein as conditioning agents include polyethylene glycols and polypropylene glycols having a molecular weight of up to about 2,000,000 such as those with CTFA names PEG-200, PEG-400, PEG-600, PEG-1000, PEG-2M, PEG-7M, PEG-14M, PEG-45M and mixtures thereof.

iii. Cationic Deposition Polymers

The hair care compositions described herein may further comprise a cationic deposition polymer. Any known natural or synthetic cationic deposition polymer can be used herein. Examples include those polymers disclosed in U.S. Pat. No. 6,649,155; U.S. Patent Application Publication Nos. 2008/0317698; 2008/0206355; and 2006/0099167, which are incorporated herein by reference in their entirety.

The cationic deposition polymer is included in the composition at a level from about 0.01 wt % to about 2 wt %, in one embodiment from about 1.5 wt % to about 1.9 wt %, in another embodiment from about 1.8 wt % to about 2.0 wt %, in view of providing the benefits of the present invention.

The cationic deposition polymer is a water soluble polymer with a charge density from about 0.5 milliequivalents per gram to about 12 milliequivalents per gram. The cationic deposition polymer used in the composition has a molecular weight of about 100,000 Daltons to about 5,000,000 Daltons. The cationic deposition polymer is a low charge density cationic polymer.

In one embodiment, the cationic deposition polymer is a synthetic cationic deposition polymer. A variety of synthetic cationic deposition polymers can be used including mono- and di-alkyl chain cationic surfactants. In one embodiment, mono-alkyl chain cationic surfactants are chosen including, for example, mono-alkyl quaternary ammonium salts and mono-alkyl amines. In another embodiment, di-alkyl chain cationic surfactants are used and include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and mixtures thereof.

In another embodiment, the cationic deposition polymer is a naturally derived cationic polymer. The term, "naturally derived cationic polymer" as used herein, refers to cationic deposition polymers which are obtained from natural sources. The natural sources may be polysaccharide polymers. Therefore, the naturally derived cationic polymer may be selected from the group comprising starches, guar, cellulose, Cassia, locust bean, Konjac, Tara, galactomannan, tapioca, and synthetic polymers. In a further embodiment, cationic deposition polymers are selected from Mirapol® 100S (Rhodia), Jaguar® C17, polyDADMAC, Tapioca starch (Akzo), Triquat™, and mixtures thereof.

4) Anionic Emulsifiers

A variety of anionic emulsifiers can be used in the hair care compositions described herein. The anionic emulsifiers include, by way of illustrating and not limitation, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxy modified polyvinyl alcohol, sulfonic acid-modified polyvinyl alcohol and phosphoric acid-modified polyvinyl alcohol, phosphated or sulfated tristyrylphenol ethoxylates.

In addition, anionic emulsifiers that have acrylate functionality may also be used in the hair care compositions described herein. Anionic emulsifiers useful herein include, but aren't limited to: poly(meth)acrylic acid; copolymers of (meth)acrylic acids and its (meth)acrylates with C1-22 alkyl, C1-C8 alkyl, butyl; copolymers of (meth)acrylic acids and (meth)acrylamide; Carboxyvinylpolymer; acrylate copolymers such as Acrylate/C10-30 alkyl acrylate crosspolymer, Acrylic acid/vinyl ester copolymer/Acrylates/Vinyl Isodecanoate crosspolymer, Acrylates/Palmeth-25 Acrylate copolymer, Acrylate/Steareth-20 Itaconate copolymer, and Acrylate/Celeth-20 Itaconate copolymer; Polystyrene sulphonate, copolymers of methacrylic acid and acrylamidomethylpropane sulfonic acid, and copolymers of acrylic acid and acrylamidomethylpropane sulfonic acid; carboxymethycellulose; carboxy guar; copolymers of ethylene and maleic acid; and acrylate silicone polymer. Neutralizing agents may be included to neutralize the anionic emulsifiers herein. Non-limiting examples of such neutralizing agents include sodium hydroxide, potassium hydroxide, ammonium hydroxide, monoethanolamine, diethanolamine, triethanolamine, diisopropanolamine, aminomethylpropanol, tromethamine, tetrahydroxypropyl ethylenediamine, and mixtures thereof. Commercially available anionic emulsifiers include, for example, Carbomer supplied from Noveon under the tradename Carbopol 981 and Carbopol 980; Acrylates/C10-30 Alkyl Acrylate Crosspolymer having tradenames Pemulen TR-1, Pemulen TR-2, Carbopol 1342, Carbopol 1382, and Carbopol ETD 2020, all available from Noveon; sodium carboxymethylcellulose supplied from Hercules as CMC series; and Acrylate copolymer having a tradename Capigel supplied from Seppic. In another embodiment, anionic emulsifiers are carboxymethylcelluloses.

5) Benefit Agents

The benefit agents comprise a material selected from the group consisting of anti-dandruff agents; perfumes; brighteners; enzymes; perfumes; sensates in one aspect a cooling agent; attractants, anti-bacterial agents; dyes; pigments; bleaches; and mixtures thereof.

In one aspect said benefit agent may comprise an anti-dandruff agent. Such anti-dandruff particulate should be physically and chemically compatible with the essential components of the composition, and should not otherwise unduly impair product stability, aesthetics or performance.

According to an embodiment, the hair care compositions may comprise an anti-dandruff active, which may be an anti-dandruff active particulate. In an embodiment, the anti-dandruff active is selected from the group consisting of: pyridinethione salts; azoles, such as ketoconazole, econazole, and elubiol; selenium sulphide; particulate sulfur; keratolytic agents such as salicylic acid; and mixtures thereof. In an embodiment, the anti-dandruff particulate is a pyridinethione salt.

Pyridinethione particulates are suitable particulate anti-dandruff actives. In an embodiment, the anti-dandruff active is a 1-hydroxy-2-pyridinethione salt and is in particulate form. In an embodiment, the concentration of pyridinethione anti-dandruff particulate ranges from about 0.01 wt % to about 5 wt %, or from about 0.1 wt % to about 3 wt %, or from about 0.1 wt % to about 2 wt %. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. Nos. 2,809,971; 3,236,733; 3,753,196; 3,761,418; 4,345,080; 4,323,683; 4,379,753; and 4,470,982.

The anti-dandruff active can be selected from polyvalent metal salts of pyrithione, the hair care compositions may further comprise one or more anti-fungal and/or anti-microbial actives. In an embodiment, the anti-microbial active is selected from the group consisting of: coal tar, sulfur, fcharcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulphide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the hair care composition, the azole anti-microbial active is included in an amount of from about 0.01 wt % to about 5 wt %, or from about 0.1 wt % to about 3 wt %, or from about 0.3 wt % to about 2 wt %. In an embodiment, the azole anti-microbial active is ketoconazole. In an embodiment, the sole anti-microbial active is ketoconazole.

The hair care compositions described herein may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the hair care compositions may comprise an effective amount of a zinc-containing layered material. In an embodiment, the composition comprises from about 0.001 wt % to about 10 wt %, or from about 0.01 wt % to about 7 wt %, or from about 0.1 wt % to about 5 wt % of a zinc-containing layered material, by total weight of the hair care composition.

The formulations of the present invention may be present in typical hair care compositions. They may be in the form of solutions, dispersion, emulsions, powders, talcs, encapsulated, spheres, spongers, solid dosage forms, foams, and other delivery mechanisms. The composition of the present invention may be hair tonics, leave-on hair products such as conditioners, treatment, and styling products, rinse-off hair products such as conditioners, shampoos, and treatment products; and any other form that may be applied to the hair and preferably applied to the scalp.

B. Method of Making the Hair Care Compositions

A process for preparing a hair care composition includes mixing all ingredients in a container, beaker, tank etc. with an overhead mixer at a medium to high rate of mixing until all ingredients are incorporated and the batch is homogenous.

The pH is adjusted to the desired value within the range of from about 2 to about 4 using an acid and conjugate base. For example, the pH may be about 2, about 3, about 4, or within a range between the recited values. According to one embodiment, the pH is adjusted with an acid to within a range from about 2 to about 4. Exemplary acids include carboxylic acids, such as citric acid, and mineral acids, such as hydrochloric acid. Suitable conjugate bases include, but are not limited to, sodium citrate.

According to another aspect, the method further includes adding a rheology modifier to the hair care composition to obtain a rheology value in the range from about 3000 cPs to about 15,000 cPs. The rheology value may be about from about 3000 cPS, about 4000 cPs, about 5000 cPs, about 6000 cPs, to about 10,000 cPs, about 13,000 cPs, about 15,000 cPs, or within a range between the recited values. Exemplary rheology modifiers include those available under the tradenames Sepigel™ 305, Simulgel™ 600, Sepimax Zen, Simulgel™ EG, Simulgel™ EPG, Simulgel™ NS, Simulgel™ A, Sepiplus™ 400, Sepiplus™ 250, Sepiplus™ 265, Aristoflex® AVC, Aristoflex® Velvet, Aristoflex® TAC, Aristoflex® HMB, Aristoflex® BLV, or Aristoflex® AVS, and combinations thereof.

C. Test Methods
1. Shine Test
   a. Wet a 6 g/general population switch for 1 minute.
   b. Treat front and back of switch with 6 mL (3 mL on each side) of the hair care composition or 0.6 mL (0.3 mL on each side) of shampoo.
   c. Massage product into switch for 30 seconds.
   d. If a hair care composition as described herein, leave on for 5 minutes then rinse for 1 minute. If a (comparative example) shampoo, rinse switch right away for 1 minute.
   e. Squidgy out excess water.
   f. Comb switch 3× and allow to dry overnight.
   g. Comb switches 6 times.
   h. Evaluate switch for shine by having 5 people evaluated switches for shine by rank ordering them from 1 to 5. 1=most shiny and 5=least shiny.
2. Combing and Hair Feel Test:
   a. Wet a 6 g/general population switch.
   b. Treat front and back of switch with 6 mL (3 mL on each side) of the hair care composition described herein.
   c. Massage product into switch (moving down the length of the switch 6 times).
   d. Let product sit on switch for "x" amount of time (0-10 minutes).
   e. Rinse switch for 1 minute.
   f. Squidgy out excess water.
   g. Comb switch 3× and allow to dry overnight.
   h. Comb switches 6 times.
   i. Evaluate switches for ease to comb and hair feel by having 5 people evaluate switches by ranking them in order from easiest to comb to hardest to comb and best hair feel to worst hair feel. A ranking of 1 equals easiest to comb/best hair feel and a ranking of 7 equals hardest to comb/worst hair feel.

Data

Figure 2:
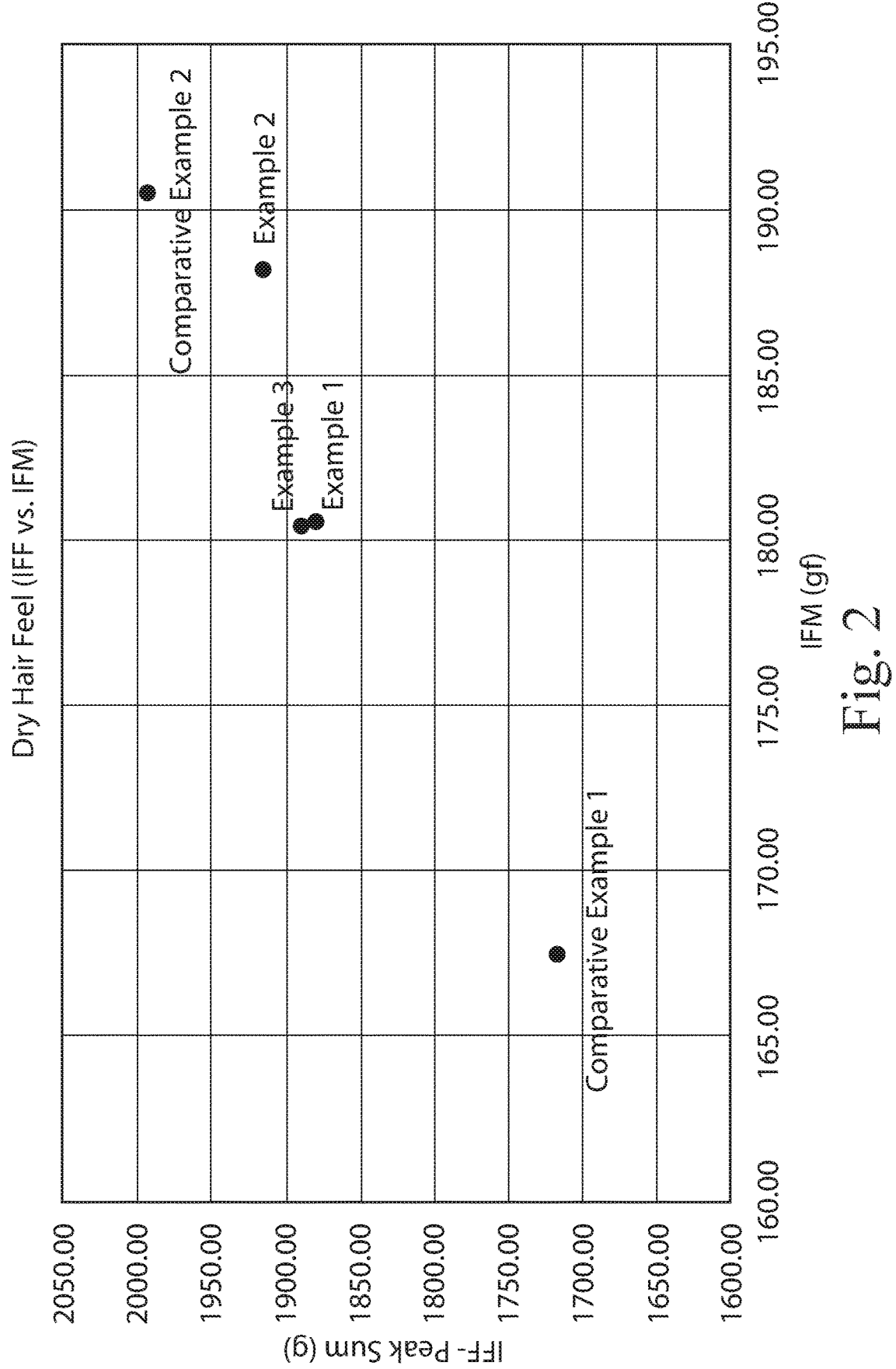
FIG. 2 is a graph showing the dry hair feel test results for hair samples after application of hair care compositions.

In Wet Feel of Examples 1, 2, and 3 perform similarly to Comparative Example 2, but Examples 1, 2, and 3 have lower work to detangle forces. Example 1 has a work to detangle force that is similar to Comparative Example 1. The data for the Examples are surprising because typically formulas that clean the hair well do not leave the hair easy to comb. Examples 1, 2, and 3 also have dry friction scores (IFF/IFM) that fall between Comparative Example 1 and Comparative Example 2. This is surprising because typically formulas that do not contain a silicone leave the hair feeling dry and stripped after washing. It is believed that the low pH of the formula is driving the cleaning, but not leaving the hair feeling stripped because it contains low amounts of surfactant. See data in FIGS. 1 and 2.
The Example 4 provides the most shine followed by comparative example 2 and comparative example 3. Comparative Example 1 has the least amount of shine.

TABLE 1

Shine Data

| Product | Panelist 1 | Panelist 2 | Panelist 3 | Panelist 4 | Panelist 5 | Average Ranking |
|---|---|---|---|---|---|---|
| No Treatment | 5 | 3 | 3 | 4 | 3 | 3.6 |
| Comparative Example 2 | 4 | 2 | 4 | 3 | 2 | 3 |
| Comparative Example 3 | 3 | 4 | 2 | 2 | 4 | 3 |
| Comparative Example 1 | 2 | 5 | 5 | 5 | 5 | 4.4 |
| Example 4 | 1 | 1 | 1 | 1 | 1 | 1 |

TABLE 2

Combing and Hair Feel Data

| Amount of Time Example 4 was left on the Hair Switch | Ranking for Ease of Combing | Rankings for Hair Feel |
|---|---|---|
| 30 seconds | 4 | 4 |
| 1 minute | | |
| 2 minutes | | |
| 3 minutes | | |
| 4 minutes | 3 | 3 |
| 5 minutes | 2 | 1 |
| 10 minutes | 1 | 2 |

Results: For the hair care compositions described herein, if the hair care composition stays on the hair for at least about 4 minutes the benefit is noticeable. If the hair care composition is on the hair for less than about 4 minutes the hair feel and combing benefits are not consumer noticeable.

Examples

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the present invention as described herein. Triethanolamine is abbreviated TEA.

EXAMPLES

| Ingredients | Comparative Example 1 | Comparative Example 2 | Comparative Example 3 | Example 1 | Example 2 | Example 3 | Example 4 |
|---|---|---|---|---|---|---|---|
| Citric Acid | 0.18% | 0.19% | | 1.00% | 1.00% | 1.00% | 2.00% |
| Salicylic Acid | | | | | | | 0.50% |
| Cocamide MEA | 1.00% | | | | | | |
| Cocamidopropyl Betaine | 6.67% | 5.00% | 3.33% | | 6.67% | 10.00% | |
| Guar Hydroxypropyltrimonium Chloride | 0.15% | | 0.23% | | | | |

-continued

| Ingredients | Comparative Example 1 | Comparative Example 2 | Comparative Example 3 | Example 1 | Example 2 | Example 3 | Example 4 |
|---|---|---|---|---|---|---|---|
| Histidine | | 0.01% | | | | | |
| Methocel 40-101 | | 0.25% | | | | | |
| Methy Tyrosinate HCl | | 0.01% | | | | | |
| Dimethicone | 1.71% | | 1.14% | | | | |
| Methylchloroisothia-zolinone/Methylisothiazolinone | 0.03% | 0.03% | 0.05% | | | | |
| PANTHENOL DL 56 SOLUTION | 0.05% | 0.09% | | | | | |
| Panthenyl Ethyl Ether | 0.03% | 0.05% | | | | | |
| Perfume | 0.65% | 1.00% | 0.85% | 0.50% | 0.50% | 0.50% | 1.00% |
| Polyquaternium-6 and Sodium Chloride | 0.32% | | | | | | |
| SLE3S | 21.43% | 21.43% | 21.43% | | | | |
| SLE1S | | | | 7.69% | | | 7.69% |
| Sodium Benzoate | 0.25% | 0.25% | 0.25% | | | | |
| Sodium Chloride | 0.00% | 0.50% | | | | | |
| Sodium citrate tribasic dihydrate | 0.00% | 0.00% | | | | | |
| Sodium HC Base | 7.50% | | 12.50% | | | | |
| Sodium Lauryl Sulfate | 18.97% | 32.76% | 15.52% | | | | |
| Sodium Xylenesulfonate (40% Solution) | 0.00% | 0.00% | 0.00% | | | | |
| Polysorbate 20 | | | | 0.20% | 0.20% | 0.20% | 0.20% |
| Polyacrylate crosspolymer-6 | | | | 1.75% | 1.75% | 2.00% | 1.75% |
| Tetrasodium EDTA Tetrahydrate | 0.16% | 0.16% | | | | | |
| Zinc Pyrithione | | | 2.50% | | | | |
| Zinc Carbonate | | | 1.61% | | | | |
| 20% Sodium Chloride Solution | | | 6.50% | | | | |
| Hydrochloric Acid | | | 0.72% | | | | |
| Water | 40.90% | 38.27% | 33.37% | 88.86% | 89.88% | 86.30% | 86.86% |
| pH | 5.5-6.5 | 5.5-6.5 | 6.5-8.3 | 2.8-3.3 | 2.8-3.3 | 2.8-3.3 | 2.8-3.3 |
| Viscosity (cps) | 7,000-11,000 | 6500-8500 | 8,000-14,000 | 6,000-12,000 | 6,000-12,000 | 6,000-12,000 | 6,000-12,000 |
| Dynamic Rinse Friction - Wet Feel (gf) | 984.14 | 1417.55 | | 1267.69 | 1335.06 | 1312.52 | |
| Combing Robot - Total Work to Detangle (N*mm) | 390.75 | 537.04 | | 406.65 | 453.28 | 512.3 | |
| IFF - Peak Sum (f) | 1717.212 | 1993.743 | | 1879.821 | 1915.857 | 1890.043 | |
| IFM (gf) | 167.463 | 190.545 | | 180.603 | 188.230 | 180.480 | |

Examples/Combinations

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of cleansing hair and scalp using an aqueous composition comprising;
    a. applying an aqueous composition to the hair and scalp, wherein the aqueous composition comprises:
    1) from about 1% to about 9% of sodium lauryl ether sulfate;
    2) from about 0.5 wt % to about 3 wt % of polyacrylate crosspolymer-6;
    3) from about 0.01% to about 5% salicylic acid;
    4) from about 80% to about 90% water;
    5) citric acid;
    6) polysorbate polysorbate-20;
    7) perfume;
    4) and wherein the pH of the aqueous composition is from about 2 to about 4, and the viscosity of the aqueous composition is from about 6,000 cP to about 9000 cP;
    and wherein the method of cleansing hair and scalp comprises the steps:

b. leaving the aqueous composition on hair from about 4 to about 15 minutes, and
c. rinsing the aqueous composition with water;

wherein the aqueous composition is free of conditioning agents selected from the group consisting of silicone oils, cationic silicones, silicone gums, silicone resins, hydrocarbon oils, polyethylene glycol, cationic deposition polymers, quaternary ammonium compounds, polyolefins, and fatty esters.

2. The method of claim 1, wherein sodium lauryl ether sulfate in the aqueous composition is from about 3 wt % to about 8 wt %.

* * * * *